United States Patent [19]

Allen et al.

[11] Patent Number: 5,377,530
[45] Date of Patent: Jan. 3, 1995

[54] APPARATUS FOR HYDROSTATIC PRESSURE TESTING OF TUBULAR PRODUCTS

[75] Inventors: Bruce F. Allen, Granby; Alfred D. DePeau, Somers, both of Conn.; David L. Crick, Chattanooga, Tenn.

[73] Assignee: Combustion Engineering, Inc., Conn.

[21] Appl. No.: 98,888

[22] Filed: Jul. 29, 1993

[51] Int. Cl.6 .............................................. G01M 3/28
[52] U.S. Cl. .................................. 73/49.5; 73/40.5 R
[58] Field of Search ................... 73/40.5 R, 49.1, 49.8, 73/49.5

[56] References Cited

U.S. PATENT DOCUMENTS

| | | | |
|---|---|---|---|
| 3,412,790 | 11/1968 | Brown | 73/40.5 R X |
| 4,460,019 | 7/1984 | Condon | 73/49.1 X |
| 4,468,952 | 9/1984 | Rathburn | 73/40.5 R |

FOREIGN PATENT DOCUMENTS

| | | | |
|---|---|---|---|
| 64137 | 4/1982 | Japan | 73/40.5 R |
| 40229 | 3/1984 | Japan | 73/40.5 R |
| 111730 | 5/1991 | Japan | 73/40.5 R |
| 127859 | 4/1950 | Sweden | 73/40.5 R |
| 762629 | 11/1956 | United Kingdom | 73/40.5 R |
| 1199919 | 7/1970 | United Kingdom | 73/40.5 R |

Primary Examiner—Hezron E. Williams
Assistant Examiner—Joseph W. Roskos
Attorney, Agent, or Firm—Ronald P. Kananen; John H. Mulholland

[57] ABSTRACT

An apparatus for hydrostatic pressure testing of tubular products that enables short segments of the tubular product to be individually tested under conditions simulating a capped tube hydrostatic test. The apparatus includes a first seal bladder and gripper member assembly connected to a second seal bladder and gripper member assembly by a connecting member that allows relative axial movement between the two assemblies. A fluid outlet port is provided in the connecting member to introduce pressurized fluid into the short segment of the tubular product between the seal bladders of the two assemblies. Since the first seal bladder and gripper member assembly is axially movable relative to the second seal bladder and gripper member assembly, an axial stress as well as a hoop stress will be induced in the tubular product during testing.

16 Claims, 5 Drawing Sheets

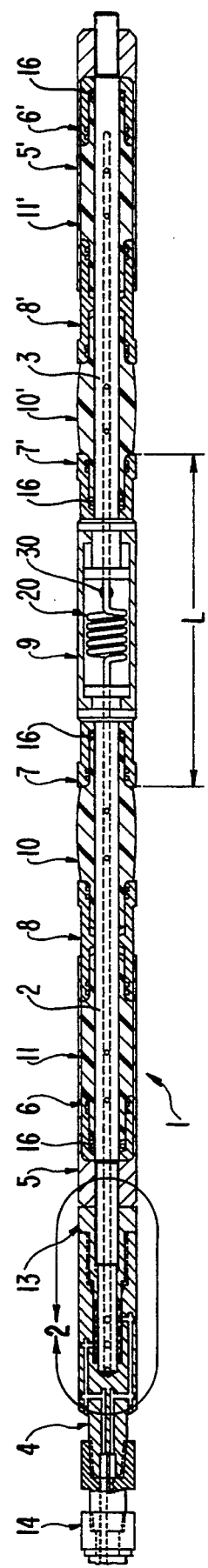

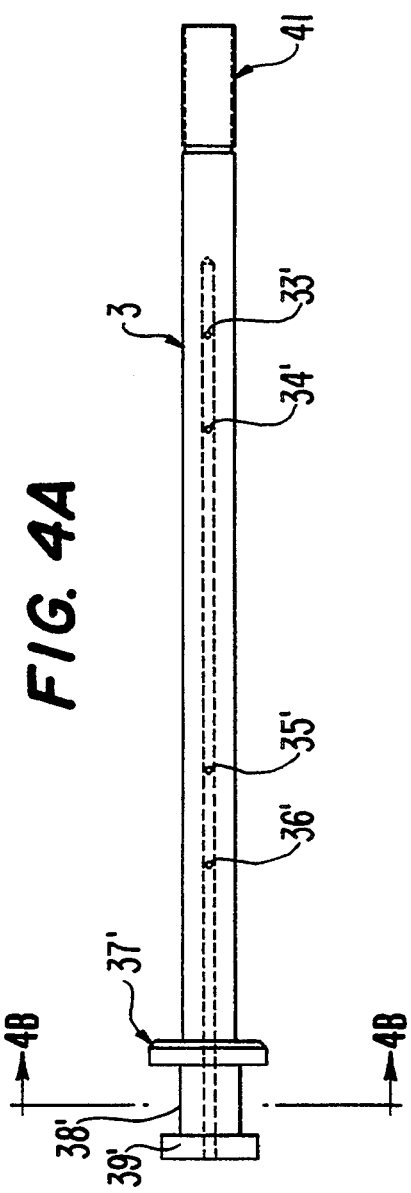
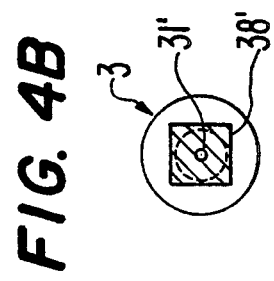

APPARATUS FOR HYDROSTATIC PRESSURE TESTING OF TUBULAR PRODUCTS

BACKGROUND OF THE INVENTION

1. Field of the Invention

The present invention relates generally to hydrostatic pressure testing of tubular products, and more specifically, to a testing apparatus for providing in situ testing of individual segments of tubular products in a manner that simulates the stresses encountered during use of the tubular product.

2. Description of the Related Art

The purpose of hydrostatic pressure testing of tubular products is to detect material defects that may affect the safe performance of the products for their intended application. This is particularly important where high operating pressures are encountered during use, or where contaminated materials (e.g., radioactive fluids) are transported through the tubular products.

Hydrostatic pressure testing of tubular products at design limit conditions is typically done by capping the tubular product at each end and pressurizing the entire tube using a fluid such as water. A major limitation of this method is that the entire product must be tested without regard to the location of any defects. Failure of the tube, if it occurs, will only reveal the location of the worst defect without allowing an independent evaluation of other possible defects along the length of the tube. In cases where multiple defects are known to exist, no acceptable method has heretofore been available to independently test each of the defects.

SUMMARY OF THE INVENTION

It is an object of the present invention to provide a hydrostatic testing apparatus which is capable of detecting and evaluating individual defects along the length of a tubular product.

It is a further object of the present invention to provide an apparatus which induces stresses in a tube that closely simulate stresses induced in the tube during a capped hydrostatic test.

It is a further object of the present invention to provide a testing apparatus capable of sealing a short segment of a tube and inducing design limit hydrostatic pressure within the short segment of the tube to evaluate possible defects therein.

It is a further object of the present invention to provide an apparatus which uses fluid pressure to activate a pair of sealing devices for sealing a short segment of a tube and a pair of gripping devices for fixing the sealing devices against axial movement within the tube.

To achieve the foregoing and other objects and in accordance with the purpose of the present invention, as embodied and broadly described herein, the testing apparatus of this invention may comprise a first seal/gripper assembly having a first seal bladder and a first gripper member connected to each other; a second seal/gripper assembly having a second seal bladder and a second gripper member connected to each other; and a connecting member attached between the first seal/gripper assembly and the second seal/gripper assembly.

A fluid port arrangement is provided for expanding each of the first and second seal bladders into sealing engagement with an inner surface of a tubular product and for expanding each of the first and second gripper members into gripping engagement with an inner surface of the tubular product.

A testing fluid supply is provided for inducing pressure within a segment of the tubular product between the first and second seal/gripper assemblies. The connecting member allows the first and second seal/gripper assemblies to move in an axial direction with respect to one another when pressure is induced into the tested segment of the tubular product, whereby stresses induced into the tested segment of the tubular product closely simulate those of a capped tube hydrostatic test.

BRIEF DESCRIPTION OF THE DRAWINGS

The present invention will become more clearly appreciated as a description of the preferred embodiment of the invention is made with reference to the appended drawings in which:

FIG. 1 is a section view of a testing apparatus according to the present invention;

FIG. 2 is an enlarged detail view of section "Z" of the testing apparatus of FIG. 1;

FIGS. 4A and 4B are front and first end views, respectively, of a second shaft for supporting components of the testing apparatus;

DESCRIPTION OF THE PREFERRED EMBODIMENT

Reference will now be made in detail to a preferred embodiment of the invention, an example of which is illustrated in the accompanying drawings.

Figure 6:
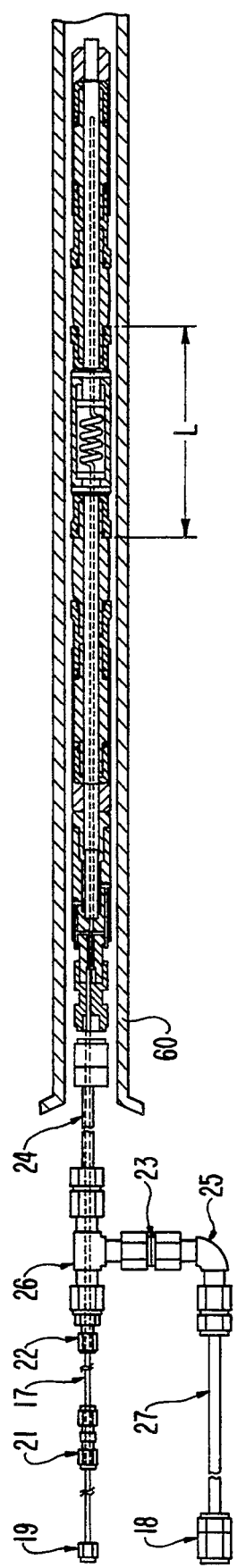
FIG. 6 is a schematic view of the testing apparatus of FIG. 1 positioned within a tube to be tested.

The hydrostatic pressure testing apparatus of the present invention is designed for use within a tubular product 1 which may, for example, take the form of a steam generator tube 60 (FIG. 6). Since it is common for high-pressure tube products to be several feet long (e.g., up to 30 feet), it is desired to provide a device which will individually evaluate short segments of the tubing to test for material defects along the entire length thereof. The present invention accomplishes this in a manner that induces stresses in individual short segments L of the tube 60 similar to those which would be experienced during normal use of the tube, and which are simulated by the typical capped tube hydrostatic test.

As shown in FIG. 1, the testing apparatus 1 includes a first mounting shaft 2 and a second mounting shaft 3 together extending substantially the entire length of the assembly and supporting various seal and gripper components (discussed below) therealong. A threaded bottom connector assembly 4 is threadedly connected to the first shaft 2 at one end thereof for directing fluid pressure into first and second longitudinally extending ports 31 and 32 in the first shaft 2.

Figure 3A:
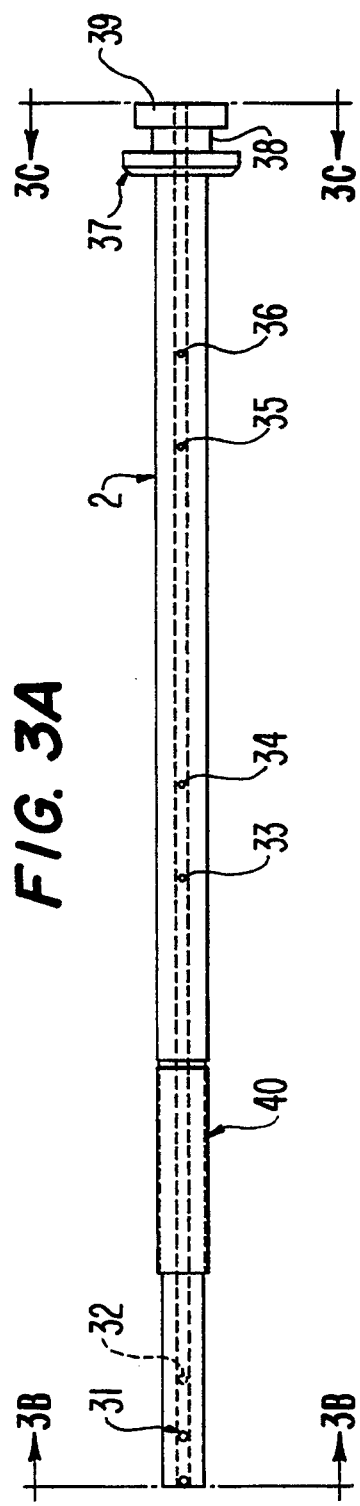
FIGS. 3A, 3B and 3C are front, first end and second end views, respectively, of a first shaft for supporting components of the testing apparatus.
Figure 3C:
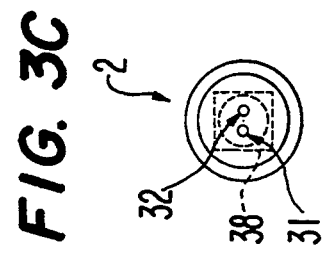
Figure 3B:

The first shaft 2 supports a first gripper member 5 and a first seal bladder 10 along a length thereof. The first seal bladder 10 is in fluid connection via ports 35 and 36 (FIG. 3A) with the first port 31 for expanding the bladder 10 when pressure is induced into the first port 31. Similarly, a first gripper bladder 11 is positioned within the first gripper member 5 for expanding a slotted thin metal wall 52 of the first gripper member 5. The gripper bladder 11 is in fluid connection via ports 33 and 34 (FIG. 3A) with port 31 for expanding the bladder 11 when pressure is induced into port 31. First, second and third cap members 6, 7 and 8, and respective O-rings 16, are provided to seal and securely mount each end of the bladders 10 and 11 to the first shaft 2.

The second shaft 3 supports a second gripper member 5' and a second seal bladder 10' along a length thereof in a substantially mirror image to the components on the first shaft 2. The second seal bladder 10' is in fluid connection via ports 35' and 36' (FIG. 4A) with a port 31' extending through the second shaft 3 for expanding the second bladder 10' when pressure is induced into the port 31'. Similarly, a second gripper bladder 11' is positioned within the second gripper member 5' for expanding a slotted thin metal wall 52 of the second gripper member 5'. The gripper bladder 11' is in fluid connection via ports 33' and 34' (FIG. 4A) with the port 31' for expanding the bladder 11' when pressure is induced into the port 31'. Cap members 6', 7' and 8', and respective O-ring seals 16, are provided to seal and securely mount each end of the bladders 10' and 11' to the second shaft 3.

A connecting member 9 connects the first shaft 2 and second shaft 3 together end-to-end in a limited movement telescoping connection. One side of the connecting member 9 is securely fixed between collars 37 and 39 (FIG. 3A) to an end of the first shaft 2. A square cross-section portion 38 of the first shaft 2 prevents rotational movement of the connecting member 9 with respect to the first shaft 2.

The other side of the connecting member 9 is telescopingly connected between collars 37' and 39' (FIG. 4A) to an end of the second shaft 3. The significance of the telescoping connection will become apparent as the operation of the invention is further explained below. A square cross-section portion 38' of the second shaft 3 prevents rotational movement of the second shaft 3 with respect to the connecting member 9 and the first shaft 2.

A tube coil 20 is provided within the connecting member 9 to provide a fluid connection between the port 31 of the first shaft 2 and the port 31' of the second shaft 3. Thus, the first seal bladder 10 and first gripper bladder 11 are in fluid connection with the second seal bladder 10' and second gripper bladder 11' for simultaneous expansion when pressurized fluid is introduced into the port 31. The tube coil 20 also preferably provides a small tension force to ensure that the second shaft 3 is retracted towards the first shaft 2 within the connecting member 9 as the testing apparatus is initially positioned for use.

As shown in FIG. 2, the bottom connector assembly 4 in the preferred embodiment includes first and second fluid ports 28 and 29 for introducing pressurized fluid into respective ports 31 and 32 of the first shaft 2. The ports 28 and 29 in the connector assembly 4 are sealingly connected via first and second separator rings 12 and 12' and respective O-ring seals 15 to the ports 31 and 32 after the connector assembly 4 is threaded via a connector insert 13 onto a threaded portion 40 of the first shaft 2.

Figure 5A:
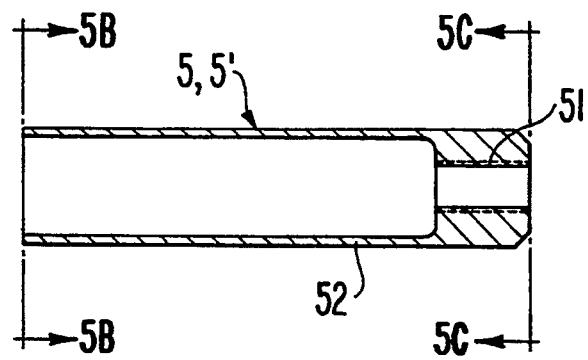
FIGS. 5A, 5B and 5C are front, first end and second end views, respectively, of a metal gripper member according to the present invention.
Figure 5B:
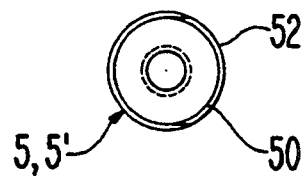
Figure 5C:
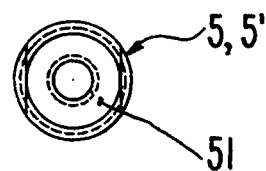

As shown in FIGS. 5A, 5B and 5C, the first and second gripper members 5 and 5' each include a threaded portion 51 for securely mounting the members to respective threaded portions 40 and 41 on the first and second shafts 2 and 3. The gripper members 5 and 5' also include a thin wall portion provided with longitudinally extending slots 50 (FIG. 5B) uniformly spaced about the circumference of the thin wall portion. The slots 50 allow controlled expansion of the thin wall portions when pressure is induced in the gripper bladders 11 and 11'.

FIG. 6 shows an assembly for connecting the testing apparatus to a source of pressurized fluid. The assembly includes a braided hose arrangement 24 of a sufficient length (e.g., up to 30 feet or more) to enable the testing apparatus to be fed into long tubes for testing. Separate fluid lines 17 and 27 are fed into the hose arrangement 24 to provide separately controlled inputs to the fluid ports 28 and 29. Appropriate couplings 18, 19 and 21, 22, 23 and 25 and union 26 are provided to connect each of the fluid lines 17 and 27 to the hose arrangement 24.

In operation, the testing apparatus of the present invention provides a convenient and very effective means to test short segments of tubular products under the same stress conditions as a typical capped tube hydrostatic test. The testing apparatus 1 is first positioned within the tube 60 such that the short segment L of the tube 60 to be tested corresponds with the portion of the testing apparatus between the first and second seal bladders 10 and 10'. Fluid is then introduced into the fluid ports 31 and 31' via port 28 and fluid line 17, thereby causing the first and second seal bladders 10 and 10' and the first and second gripper bladders 11 and 11' to expand under fluid pressure.

Upon expansion, the first and second seal bladders 10 and 10' sealingly engage an inner surface of the tube 60. Similarly, the first and second gripper members 5 and 5' are forced into engagement with the inner surface of the tube 60 by the expanding first and second gripper bladders 11 and 11'. Since the gripper members 5 and 5' are made of metal, or similar material, their engagement with the inner surface of the tube 60 provides a very effective gripping action (e.g., metal-to-metal engagement) that prevents axial movement of the testing assembly with respect to the tube.

After each of the gripper members 5 and 5' and the seal bladders 10 and 10' are expanded into gripping and sealing engagement, respectively, with the inner surface of the tube 60, a testing fluid is introduced into the second fluid port 32 via port 29 and fluid line 27. The fluid port 32 directs the testing fluid into the short segment of the tube 60 via an outlet port 30 in the connecting member 9. The testing fluid is restricted within the short segment L of the tube 60 by the expanded first and second seal bladders 10 and 10'.

Since the second shaft 3 is axially movable with respect to the connecting member 9, and hence the first shaft 2, an axial stress will be induced in the walls of the tube 60 due to an effective axial fluid force tending to force the components on the first shaft 2 away from the components on the second shaft 3. Thus, axial stresses as well as hoop stresses will be applied to the tube 60 when the testing fluid is pressurized. In practice, the axial expansion of the testing apparatus 1 during testing will only amount to a small fraction of an inch. However, this small amount enables stresses similar to those induced during a typical capped tube hydrostatic test to be developed in the short segment of the tube 60.

It will be appreciated that the present invention is not limited to the structures disclosed above and that a number of variations are possible without departing from the scope of the present invention. It is intended that the scope of the claims only be limited by the claims appended hereto.

What is claimed is:

1. An apparatus for hydrostatic pressure testing tubular products, comprising:
    a first seal/gripper assembly having a first seal bladder and a first gripper member connected to each other;
    a second seal/gripper assembly having a second seal bladder and a second gripper member connected to each other;
    a connecting member attached between said first seal/gripper assembly and said second seal/gripper assembly;
    means for expanding each of said first and second seal bladders into sealing engagement with an inner surface of a tubular product;
    means for expanding each of said first and second gripper members into gripping engagement with an inner surface of the tubular product; and
    means for inducing pressure within a segment of the tubular product between said first and second seal/gripper assemblies;
    wherein said means for expanding each of said gripper members includes a gripper bladder positioned within each of said gripper members and a fluid pressure supply line in fluid communication with each of said gripper bladders.

2. A testing apparatus as set forth in claim 1, wherein said pressure inducing means includes a hydrostatic pressure supply line in fluid communication with a fluid outlet port in said connecting member.

3. An apparatus for hydrostatic pressure testing tubular products, comprising:
    a first seal/gripper assembly having a first seal bladder and a first gripper member connected to each other;
    a second seal/gripper assembly having a second seal bladder and a second gripper member connected to each other;
    a connecting member attached between said first seal/gripper assembly and said second seal/gripper assembly;
    means for expanding each of said first and second seal bladders into sealing engagement with an inner surface of a tubular product;
    means for expanding each of said first and second gripper members into gripping engagement with an inner surface of the tubular product; and
    means for inducing pressure within a segment of the tubular product between said first and second seal/gripper assemblies;
    wherein said first and second seal/gripper assemblies are movable relative to one another in an axial direction.

4. A testing apparatus as set forth in claim 3, wherein said means for expanding each of said seal bladders includes a fluid pressure supply line in fluid communication with each of said seal bladders.

5. An apparatus for hydrostatic pressure testing tubular products, comprising:
    a first seal member expandable into sealing engagement with an inner surface of a tubular product;
    a first gripper member adjacent to said first seal member, said first gripper member expandable into gripping engagement with the inner surface of the tubular product;
    a second seal member spaced from said first seal member, said second seal member expandable into sealing engagement with the inner surface of the tubular product;
    a second gripper member adjacent to said second seal member, said second gripper member expandable into gripping engagement with the inner surface of the tubular product; and
    a connector member connecting said first and second seal members, said connector member having a fluid port for introducing pressurized fluid into the tubular product between said first and second seal members;
    wherein said first gripper and seal members are movable in an axial direction with respect to said second gripper and seal members.

6. A testing apparatus as set forth in claim 5, wherein said first and second seal members comprise first and second seal bladders in fluid communication with a fluid pressure supply line.

7. A testing apparatus as set forth in claim 6, wherein first and second gripper bladders are provided within said first and second gripper members, respectively, said first and second gripper bladders being in fluid communication with a fluid pressure supply line.

8. A testing apparatus as set forth in claim 7, wherein said first and second seal bladders are in fluid communication with said first and second gripper bladders, whereby said seal bladders and gripper members simultaneously expand into engagement with the inner surface of the tubular product when pressure is induced through said fluid pressure supply line.

9. A testing apparatus as set forth in claim 5, further comprising a first shaft fixedly supporting said first gripper and seal members, a second shaft fixedly supporting said second gripper and seal members, and a tube coil extending between a fluid port of said first shaft and a fluid port of said second shaft for supplying fluid pressure to said second seal and gripper members.

10. A testing apparatus as set forth in claim 9, wherein said tube coil provides a tension force to bias said first and second shafts towards a retracted state with respect to each other.

11. A testing apparatus as set forth in claim 9, wherein said connecting member prevents said first and second shafts from rotation relative to each other while permitting axial movement of said first and second relative to each other.

12. An apparatus for hydrostatic pressure testing tubular products, comprising:
    a first shaft;
    a first seal member mounted to said first shaft and expandable into sealing engagement with an inner surface of a tubular product;
    a second shaft;
    a second seal member mounted to said second shaft and expandable into sealing engagement with the inner surface of the tubular product;
    a connector member connecting said first and second shafts, said connector member allowing limited axial movement between said first and second shafts and having a fluid port for introducing pressurized fluid into the tubular product between said first and second seal members; and
    a first gripper member mounted to said first shaft and a second gripper member mounted to said second shaft, said first and second gripper members being expandable into gripping engagement with the inner surface of the tubular product.

13. A testing apparatus as set forth in claim 12, further comprising a tube coil within said connector member, said tube coil connected between a fluid port of said first shaft and a fluid port of said second shaft for supplying fluid pressure to said second seal and gripper members.

14. A testing apparatus as set forth in claim 13, wherein said tube coil provides a tension force to bias said first and second shafts towards a retracted state with respect to each other.

15. A testing apparatus as set forth in claim 12, wherein said first and second seal members comprise first and second seal bladders, respectively, in fluid communication with a fluid pressure supply line.

16. A testing apparatus as set forth in claim 15, further comprising first and second gripper bladders provided within said first and second gripper members, respectively, said gripper bladders being in fluid communication with said fluid pressure supply line.

* * * * *